United States Patent
Ionkin

(10) Patent No.: US 6,455,723 B1
(45) Date of Patent: Sep. 24, 2002

(54) AMINONITRILE PRODUCTION

(75) Inventor: Alex Sergey Ionkin, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/682,656

(22) Filed: Oct. 2, 2001

(51) Int. Cl.⁷ ............................................. C07C 255/00
(52) U.S. Cl. ...................................... 558/459
(58) Field of Search ......................... 558/459

(56) References Cited

U.S. PATENT DOCUMENTS

| | | | |
|---|---|---|---|
| 2,208,598 A | 7/1940 | Rigby | |
| 2,257,814 A | 10/1941 | Rigby | |
| 2,762,835 A | 9/1956 | Swerdloff | |
| 3,322,815 A | 5/1967 | Feldman et al. | |
| 3,350,439 A | 10/1967 | Feldman et al. | |
| 3,591,618 A | 7/1971 | Hanschke et al. | |
| 4,389,348 A | 6/1983 | Diamond et al. | |
| 4,601,859 A | 7/1986 | Galle et al. | |
| 5,151,543 A | 9/1992 | Ziemecki | |
| 5,296,628 A | 3/1994 | Sanchez | |
| 5,512,697 A | 4/1996 | Schnurr et al. | |
| 5,527,946 A | 6/1996 | Flick et al. | |
| 5,986,127 A | * 11/1999 | Ionkin et al. | ................ 558/459 |
| 6,080,884 A | 6/2000 | Ziemecki et al. | |

FOREIGN PATENT DOCUMENTS

| | | |
|---|---|---|
| DE | 836 938 | 4/1952 |
| DE | 848 654 | 9/1952 |
| DE | 19636768 A1 | 12/1998 |
| JP | 9040630 A | 2/1997 |
| WO | WO 00/64862 | 11/2000 |

* cited by examiner

*Primary Examiner*—T. A. Solola
*Assistant Examiner*—Joseph Murray
(74) *Attorney, Agent, or Firm*—Bart E. Lerman

(57) ABSTRACT

Provided is a selective hydrogenation process for producing aminonitriles by contacting the corresponding dinitriles with a hydrogen-containing fluid in the presence of a hydrogenation catalyst, a solvent and divalent sulfur and selenium compounds.

20 Claims, No Drawings

AMINONITRILE PRODUCTION

BACKGROUND OF INVENTION

Field of the Invention

The invention relates to a selective hydrogenation process for producing aminonitriles in the presence of divalent sulfur and selenium compounds.

Aminonitriles are a class of important chemicals that have a variety of industrial applications. For example, aminonitriles can be used as monomers for producing high molecular weight polyamides. Specifically, 6-aminocapronitrile can be used to produce nylon 6.

Aminonitriles can be produced by catalytic partial hydrogenation of dinitriles. See, for example, U.S. Pat. Nos. 2,208,598, 2,257,814, 2,762,835, 3,322,815, 3,350,439, 3,591,618, 4,389,348, 4,601,859, 5,151,543, 5,296,628, 5,512,697, 5,527,946, 5,986,127, 6,080,884, DE836938, DE848654, DE-A-19636768, JP-A-9040630 and WO00/64862, all of which are incorporated by reference herein for all purposes as if fully set forth. However, the yield of and selectivity to a desired aminonitrile using some of the known processes may not be as high as desired, and the amount of the complete hydrogenation product (diamine) is also generally higher than desired.

U.S. Pat. No. 5,986,127 and WO00/64862 mentioned above describe the use of certain additives in the partial hydrogenation process to improve the yield of and/or selectivity to the desired aminonitrile product, and/or reduce the amount of fully hydrogenated product (diamine) produced.

We have now found new classes of compounds that also effectively function as improved yield and/or selectivity additives in the partial hydrogenation processes such as, for example, those mentioned in previously incorporated references.

SUMMARY OF INVENTION

In accordance with one aspect of the present invention, there is provided a process for the partial hydrogenation of a dinitrile to an aminonitrile, comprising the step of contacting the dinitrile with a hydrogen-containing fluid in the presence of (a) a solvent comprising liquid ammonia, an alcohol, or both; (b) a hydrogenation catalyst; and (c) an additive comprising a compound selected from the group consisting of a divalent sulfur and a divalent selenium compound.

In accordance with another aspect of the present invention, there is provided an improved process for preparing an aminonitrile from a corresponding dinitrile by contacting the dinitrile with a hydrogen-containing fluid in the presence of a solvent and a hydrogenation catalyst, wherein the improvement comprises contacting the dinitrile, hydrogen-containing fluid, solvent and hydrogenation catalyst in the further presence of an additive comprising a compound selected from the group consisting a divalent sulfur and a divalent selenium compound.

Another aspect of the present invention relates to a method for improving the yield of and/or selectivity to an aminonitrile obtained by partially hydrogenating a corresponding dinitrile with a hydrogen-containing fluid in the presence of a solvent and a hydrogenation catalyst, comprising the step of partially hydrogenating the dinitrile in the further presence of an effective amount of an additive comprising a compound selected from the group consisting a divalent sulfur and a divalent selenium compound.

In yet another aspect of the present invention, there is provided a catalyst composition comprising a combination of (1) a hydrogenation catalyst suitable for hydrogenating a dinitrile to an aminonitrile; and (2) an additive comprising a compound selected from the group consisting of a divalent sulfur and a divalent selenium compound.

An advantage of this invention is that an aminonitrile can be produced in higher yield and/or having a higher selectivity to the aminonitrile with the additive than without.

These and other features and advantages of the present invention will be more readily understood by those of ordinary skill in the art from a reading of the following detailed description. It is to be appreciated that certain features of the invention which are, for clarity, described below in the context of separate embodiments, may also be provided in combination in a single embodiment. Conversely, various features of the invention which are, for brevity, described in the context of a single embodiment, may also be provided separately or in any subcombination.

DETAILED DESCRIPTION

According to this invention, a dinitrile is contacted with a hydrogen-containing fluid in the presence of a solvent, a catalyst and a divalent sulfur and selenium compound.

Suitable dinitriles for use herein have the general formula $R(CN)_2$, wherein R is a hydrocarbylene group selected from the group consisting of an alkylene, arylene, alkenylene, alkarylene and aralkylene group. One dinitrile or combinations of different dinitriles may be used. Preferred hydrocarbylene groups contain from 2 to 25, more preferably 2 to 15, and most preferably 2 to 10 carbon atoms per group. In other words, preferred dinitriles contain from 4 to 27, more preferably 4 to about 17, and most preferably 4 to 12, carbon atoms per dinitrile molecule. The preferred type of hydrocarbylene group is an alkylene group.

Examples of suitable dinitriles include, but are not limited to, adiponitrile; methylglutaronitrile; alpha,omega-pentanedinitrile; alpha,omega-heptanedinitrile; alpha,omega-nonanedinitrile; alpha,omega-dodecanedinitrile; alpha,omega-pentadecanedinitrile; alpha,omega-icosanedinitrile; alpha,omega-tetracosanedinitrile; 3-methylhexanedinitrile; 2-methyl-4-methyleneoctanedinitrile; and combinations of two or more thereof.

Preferably the carbon atoms of the starting dinitrile are arranged in a branched or linear chain. Preferred examples are adiponitrile (hydrogenated to 6-aminocapronitrile), methylglutaronitrile (hydrogenated to two isomeric aminonitriles: 5-amino-2-methylvaleronitrile and 5-amino-4-methyl-valeronitrile) and alpha,omega-dodecanedinitrile (hydrogenated to the corresponding aminonitrile). The preferred dinitrile is adiponitrile because its selective hydrogenation product, 6-aminocapronitrile, is a well-known monomer for polymerization applications.

Any hydrogen-containing fluid can be used in the invention as long as there is sufficient hydrogen in the fluid to selectively hydrogenate a dinitrile to an aminonitrile. The term fluid refers to liquid, gas or both. The hydrogen content in the fluid can range from 1 to 100%, preferably about 50 to about 100%, and most preferably 90 to 100% by volume. The presently preferred hydrogen-containing fluid is substantially pure hydrogen gas.

The molar ratio of hydrogen (in the hydrogen-containing fluid) to dinitrile is not critical as long as sufficient hydrogen is present to produce the desired aminonitrile. Hydrogen is generally used in excess. Hydrogen pressures are generally in the range of about 50 to about 2000 psig (about 0.45 to about 13.89 MPa), with from about 200 to about 1000 psig (about 1.48 to about 7.00 MPa) preferred.

Any solvent that comprises either liquid ammonia or an alcohol can be used in the invention. The concentration of liquid ammonia in the solvent can range from about 20 to about 100%, preferably about 50 to about 100%, and most preferably about 80% to about 100%, by weight of total solvent. A substantially pure liquid ammonia is preferred. However, if an alcohol is also present in the solvent, the concentration of ammonia can be adjusted based on the quantity of alcohol used, which is discussed in further detail below. The molar ratio of ammonia to dinitrile is preferably about 1:1 or greater, and is generally in the range of from about 1:1 to about 30:1, more preferably from about 2:1 to about 20:1.

Any alcohol that can facilitate the selected hydrogenation of a dinitrile to an aminonitrile can be used in this invention. Preferred are alcohols with 1 to 10, more preferably 1 to 4, carbon atoms per molecule. Examples of suitable alcohols include, but are not limited to, methanol, ethanol, propanol, isopropyl alcohol, butanol, isobutyl alcohol, pentanol, hexanol, heptanol, octanol, nonanol, decanol, and combinations of two or more thereof. The most preferred alcohol (when used) is methanol. The alcohol can generally be present in the solvent in the concentration of from about 20 to about 100%, preferably about 30 to about 99%, by weight based on the total solvent weight.

Typically when an alcohol is use, the solvent further comprises a base that is substantially soluble in the solvent. The term substantially refers to more than trivial. Preferred bases are ammonia, an ammonium base or an inorganic base such as, for example, alkali metal oxides, alkaline earth metal oxides, alkali metal hydroxides, alkaline earth metal hydroxides, partially neutralized acids in which one or more protons of the acids are replaced with ammonium ion, alkali metal ions, alkaline earth metal ions, or combinations of two or more thereof. Specific examples of suitable bases include, but are not limited to ammonia, lithium hydroxide, sodium hydroxide, potassium hydroxide, sodium bicarbonate, sodium carbonate, potassium bicarbonate, or combinations of two or more thereof. The most preferred bases are ammonia, lithium hydroxide and sodium hydroxide for they are readily available and inexpensive.

A base can be present in the solvent in any quantity so long as the quantity can facilitate the selective hydrogenation of a dinitrile to an aminonitrile. Generally, a base can be present in the solvent in the range of from about 0.1 to about 10 weight %, based on the total weight of the starting dinitrile.

The catalyst in the process is a hydrogenation catalyst suitable for hydrogenating a dinitrile to an aminonitrile. Preferred are catalysts based on transition metals selected from the group consisting of iron, cobalt, nickel, rhodium and combinations thereof. The catalyst may also contain one or more promoters in addition to the transition metals mentioned above, for example, one or more of Group VIB and Group VII metals such as chromium, molybdenum and tungsten. The catalyst can also be in the form of an alloy, including a solid solution of two or more metals, or an individual metal.

The catalytic metal can also be supported on an inorganic support such as alumina, magnesium oxide and combinations thereof. The metal can be supported on an inorganic support by any means known to one skilled in the art such as, for example, impregnation, coprecipitation, ion exchange, and combinations of two or more thereof. The preferred inorganic support is magnesium oxide, and the preferred supported catalyst is a magnesium oxide supported nickel-iron catalyst.

The catalyst can be present in any appropriate physical shape or form. It can be in fluidizable forms, extrudates, tablets, spheres or combinations of two or more thereof. The catalyst may be in sponge metal form, for example, the Raney® nickels and Raney® cobalts. The molar ratio of catalyst to dinitrile can be any ratio as long as the ratio can catalyze the selective hydrogenation of a dinitrile. The weight ratio of catalyst to dinitrile is generally in the range of from about 0.0001:1 to about 1:1, preferably about 0.001:1 to about 0.5:1. If the catalytic metal is supported on an inorganic support or is a portion of alloy or solid solution, the catalytic metal is generally present in the range of from about 0.1 to about 60, preferably about 1 to about 50, and most preferably about 2 to about 50 weight %, based on the total catalyst weight.

The preferred catalyst is a sponge metal type catalyst. The metallic component is iron, cobalt, nickel or combinations thereof. Commercially available catalysts of this type are promoted or unpromoted Raney® Ni or Raney® Co catalysts that can be obtained from the Grace Chemical Co. (Columbia, Md.), or alternative sponge metal catalysts available, for example, from Activated Metals Corporation (Sevierville, Tenn.) or Degussa (Ridgefield Park, N.J.).

In the case of the preferred supported nickel/iron catalyst, the rate of adiponitrile conversion increases with the amount of Ni deposited on the support. The preferred concentration of Ni is between about 5 and about 50 weight %, and especially between about 25 and about 35 weight %, based on the catalyst weight (metals+support). The preferred concentration of Fe is between about 0.2 and about 20 weight %, and especially between about 0.5 and about 10 weight %, based on the catalyst weight (metals+support).

Further details on the above components can be found from various of the previously incorporated references. Specific reference may be had, for example, to U.S. Pat. Nos. 2,208,598, 2,257,814, 2,762,835, 3,322,815, 5,151,543, 5,296,628, 5,512,697, 5,527,946, 5,986,127, 6,080,884 and WO00/64862.

A wide variety of divalent sulfur and selenium compounds have been found that can effect the selectivity/yield improvement in the invention.

The term improvement is referred to as enhanced selectivity to aminonitrile product at conversions greater than about 70%, preferably conversions greater than about 80%, and especially conversions greater than about 90%, as compared to the selectivity without the use of the additive of this invention. An effective amount of the additive is amount required to achieve the aforementioned enhanced selectivity and/or an improved overall yield of aminonitrile, as compared to without the use of the additive.

As used herein, the term divalent sulfur and selenium compounds means compounds containing divalent sulfur and/or selenium compounds in the form S—, S═, —Se— and Se═. This can include a wide variety of organic and inorganic compounds, but preferred are tetraalkylammonium polysulfides and sulfide compounds, thio or dithiocarbonyl compounds and selenoaromatic compounds.

Preferred tetraalkylammonium polysulfides and sulfide compounds are those wherein the alkyl groups of the tetraalkylammonium groups each individually contain from 1 to 8 carbon atoms, and more preferably 1–4 carbon atoms. It is preferred that all four of the alkyl groups in a molecule are the same, but mixtures having different tetraalkyl substituents are suitable for use herein.

Examples of suitable tetraalkylammonium polysulfides and sulfide compounds include, but are not limited to, tetramethylammonium sulfide, tetraethylammonium sulfide, tetrapropylammonium sulfide, tetrabutylammonium sulfide and tetrabutylammonium hexasulfide. As indicated above, combinations of two or more tetraalkylammonium polysulfides and sulfide compounds are also suitable.

Examples of suitable thio or dithiocarbonyl compounds include, but are not limited to, tetramethylthiourea, dimethylthioformamide, carbon disulfide, sodium diethyldithiocarbamide and zinc diethyldithiocarbamide.

Examples of suitable selenoaromatic compounds include, but are not limited to, selenophene and its alkyl or aryl substituted derivatives; 1,3-selenazole and its alkyl and aryl substituted derivatives; and 1,2,3-selenadiazole and its alkyl and aryl substituted derivatives. Suitable alkyl substituents include $C_1$ to $C_8$ straight chain, branched or cylic alkyl groups. Suitable aryl substituents include phenyl or alkyl substituted phenyl.

The additive is present during the contacting in any quantity that can improve the selective hydrogenation of a dinitrile to its corresponding aminonitrile (e.g., an effective amount). Generally, the weight ratio of the additive to the catalyst is in the range of from about 0.01:1 to about 5:1, preferably about 0.05:1 to about 3:1, more preferably about 0.1:1 to 2:1, and especially about 0.1:1 to about 1:1.

The catalyst and additive can be separately introduced into contact with a dinitrile; however, it is preferred that the catalyst, whether it is in its metal form or in an alloy or solid solution or on an inorganic support, is precontacted with the additive. This may be done in a solvent such as, for example, an alcohol, ether, ester, ammonia or combinations of two or more thereof. Further preferably the precontacting is also carried out in a hydrogen-containing fluid such as described above. Contacting of the catalyst and additive produces a pretreated catalyst. The pretreated catalyst can be washed with a solvent disclosed above, preferably under anaerobic condition to produce an additive-treated catalyst.

The contacting of the catalyst and additive can be carried out under any conditions effective to produce an additive-treated catalyst that can improve selective hydrogenation of a dinitrile or the selectivity to an aminonitrile. Generally, the entire process for producing the additive-treated catalyst can be carried out by contacting a catalyst with an additive disclosed above at a temperature in the range of from about 20° C. to about 150° C., preferably about 30° C. to about 100° C., under the same general pressures as described above, for about 5 seconds to about 25 hours.

The partial hydrogenation process of the present invention can be carried out at a temperature in the range of from about 25 to about 150° C., preferably about 40 to about 100° C., most preferably about 60 to about 80° C., at a total pressure generally in the range of about 50 to about 2000 psig (about 0.45 to about 13.89 MPa), with from about 200 to about 1000 psig (about 1.48 to about 7.00 MPa) preferred, for a time period generally in the range of from about 15 minutes to about 25 hours, preferably about 1 hour to about 10 hours.

The process of the invention can be operated batch wise or continuously in an appropriate reactor. Stirring or agitation of the reaction mixture can be accomplished in a variety of ways known to those skilled in the art. The partial hydrogenation of the starting dinitrile to its corresponding aminonitrile with high selectivity at high conversions of the dinitrile makes this process efficient and useful.

Further general and specific process details can be found from various of the previously incorporated references. Specific reference may be had, for example, to U.S. Pat. Nos. 2,208,598, 2,257,814, 2,762,835, 3,322,815, 5,151,543, 5,296,628, 5,512,697, 5,527,946, 5,986,127, 6,080,884 and WO00/64862.

The following examples further illustrate the process of the invention and are not to be construed to unduly limit the scope of the invention.

The meaning of terms used in the Examples is defined as follows: Yield of aminonitrile is the measured concentration of aminonitrile divided by the starting concentration of dinitrile.

Conversion of the dinitrile is the difference between the starting and the instant concentration of dinitrile, divided by the starting concentration of dinitrile.

Selectivity to aminonitrile is the measured yield of aminonitrile divided by conversion of the dinitrile at that instance.

Comparative Example 1

A sponge Ni catalyst (1.2 g) promoted with Fe and Cr (Activated Metals, A4000, without any further additives) was added to a 50 cc autoclave together with 3.2 g adiponitrile (ADN) and 35 cc of liquid ammonia to form a mixture. Hydrogen was introduced to the autoclave and the ADN was hydrogenated at 60° C. under the total pressure of 1045 psig (7.31 MPa) at ca. 1500 rpm. Total conversion of ADN was reached within 30 minutes on stream. The maximum yield of aminocapronitrile was 57% at 90% ADN conversion for a selectivitiy of 63%.

Comparative Example 2

To a 300 cc autoclave, was charged 7.7 g Raney® Co (obtained from W.R. Grace Co., catalog number 2724), 0.77 g water, 26 g ADN, and 139 g liquid ammonia. The content was hydrogenated at 70° C., under the total pressure of 1000 psig (7.00 MPa) at 1000 rpm. Total conversion of ADN was reached within 40 minutes on stream. The maximum yield of aminocapronitrile was 58% at 90% ADN conversion for a selectivity of 64%.

Comparative Example 3

To a 50 cc autoclave, was charged 1.2 g of a 5% rhodium on alumina catalyst (obtained from Engelhard), 3.2 g ADN, and 35 ml liquid ammonia. The content was hydrogenated at 80° C., under the total pressure of 1060 psig (7.41 MPa), at 1500 rpm. Total conversion of AND was reached within 30 minutes on stream. The maximum yield of aminocapronitrile was 41% at 96% ADN conversion, with the major product being hexamethylene diamine.

EXAMPLE 1

1.2 g of sponge Ni catalyst (Degussa BLM 112W) was charged into a 50 cc autoclave, together with 0.05 g of tetraethylammonium hydrogen sulfide. Subsequently, 35 ml of liquid ammonia was added, and the mixture was heated to 80° C. with stirring. The pressure was adjusted to 972 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1000 psig (7.00 MPa). After 120 minutes, the yield of 6-aminocapronitrile reached ca. 78% at 95% ADN conversion for a selectivity of 82%.

EXAMPLE 2

1.2 g of sponge Ni catalyst (Degussa BLM 112W) was charged into a 50 cc autoclave, together with 0.12 g of tetraethylammonium hydrogen sulfide, 1.2 g of ADN and 35 ml of liquid ammonia was added. The mixture was heated to 80° C., and reacted with hydrogen at a total pressure of 1003 psig (7.00 MPa). After 6 hours the yield of 6-aminocapronitrile reached ca. 76% at 97% ADN conversion for a selectivity of 78%.

EXAMPLE 3

1.2 g of a 5% rhodium on alumina catalyst (obtained from Engelhard) was charged into a 50 cc autoclave, together with 0.0135 g of tetraethylammonium hydrogen sulfide. Subsequently 35 cc of liquid ammonia was added, and the mixture was heated to 80° C. with stirring. The pressure was adjusted to 1000 psig (7.00 MPa) with hydrogen, then kept under such conditions for 1.0 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1000 psig (7.43 MPa). After 27 minutes the yield of 6-aminocapronitrile reached 75% at 95% ADN conversion for a selectivity of 79%.

EXAMPLE 4

1.2 g of a 5% rhodium on alumina catalyst (obtained from Engelhard) was charged into a 50 cc autoclave, together with 0.009 g of tetraethylammonium hydrogen sulfide. Subsequently 35 cc of liquid ammonia was added, and the mixture was heated to 80° C. with stirring. The pressure was adjusted to 1045 psig (7.00 MPa) with hydrogen, then kept under such conditions for 1.0 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1045 psig (7.43 MPa). After 10 minutes the yield of 6-aminocapronitrile reached 74% at 94% ADN conversion for a selectivity of 79%.

EXAMPLE 5

1.2 g of a 5% rhodium on alumina catalyst (obtained from Engelhard) was charged into a 50 cc autoclave, together with 0.004 g of tetraethylammonium hydrogen sulfide. Subsequently 35 cc of liquid ammonia was added, and the mixture was heated to 80° C. with stirring. The pressure was adjusted to 1045 psig (7.00 MPa) with hydrogen, then kept under such conditions for 1.0 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1045 psig (7.43 MPa). After 6 minutes the yield of 6-aminocapronitrile reached 73% at 92% ADN conversion for a selectivity of 79%.

EXAMPLE 6

1.2 g of sponge Ni catalyst (Degussa BLM 112W) was charged into a 50 cc autoclave, together with 0.05 g of tetrabutylammonium hexasulfide. Subsequently, 35 ml of liquid ammonia was added, and the mixture was heated to 80° C. with stirring. The pressure was adjusted to 1044 psig (7.00 MPa) with hydrogen, and the autoclave was kept under such conditions for 1 hr. After cooling, the liquid phase was filtered off, leaving the pretreated catalyst inside of the autoclave. 1.2 g of ADN was injected into the autoclave and 35 ml of liquid ammonia was added. The mixture was heated to 80° C., and reacted with hydrogen at a total pressure of 1044 psig (7.43 MPa). After 200 minutes the yield of 6-aminocapronitrile reached ca. 76% at 95% ADN conversion for a selectivity of 80%.

EXAMPLE 7

1.2 g of sponge Ni catalyst (Degussa BLM 112W) was charged into a 50 cc autoclave, together with 0.12 g tetrabutylammonium hexasulfide, 1.2 g of ADN and 35 ml of liquid ammonia was added. The mixture was heated to 80° C., and reacted with hydrogen at a total pressure of 1054 psig (7.00 MPa). After 170 minutes the yield of 6-aminocapronitrile reached ca. 76% at 96% ADN conversion for a selectivity of 79%.

EXAMPLE 8

1.2 g of sponge Ni catalyst (Degussa BLM 112W) was charged into a 50 cc autoclave, together with 3.2 g of ADN and 0.08 g of tetramethylthiourea. Subsequently, 35 ml of liquid ammonia was added. The mixture was heated to 80° C., and reacted with hydrogen at a total pressure of 1054 psig (7.00 MPa). After 80 minutes, the yield of 6-aminocapronitrile reached ca. 73% at 91% ADN conversion for a selectivity of 80%.

EXAMPLE 9

1.2 g of sponge Ni catalyst (Degussa BLM 112W) was charged into a 50 cc autoclave, together with 3.2 g of ADN and 0.05 g of tetramethylthiourea. Subsequently, 35 ml of liquid ammonia was added. The mixture was heated to 80° C., and reacted with hydrogen at a total pressure of 1054 psig (7.00 MPa). After 14 minutes, the yield of 6-aminocapronitrile reached ca. 71% at 90% ADN conversion for a selectivity of 79%.

EXAMPLE 10

1.2 g of sponge Ni catalyst (Degussa BLM 112W) was charged into a 50 cc autoclave, together with 3.2 g of ADN and 0.05 g of dimethylthioformamide. Subsequently, 35 ml of liquid ammonia was added. The mixture was heated to 80° C., and reacted with hydrogen at a total pressure of 1060 psig (7.00 MPa). After 60 minutes, the yield of 6-aminocapronitrile reached ca. 70% at 90% ADN conversion for a selectivity of 78%.

EXAMPLE 11

1.2 g of sponge Ni catalyst (Degussa BLM 112W) was charged into a 100 cc autoclave, together with 12 g of ADN and 0.02 g of thiourea. Subsequently, 65 ml of liquid ammonia was added. The mixture was heated to 80° C., and reacted with hydrogen at a total pressure of 1000 psig (7.00 MPa). After 200 minutes, the yield of 6-aminocapronitrile reached ca. 69% at 87% ADN conversion for a selectivity of 79%.

EXAMPLE 12

1.2 g of sponge Ni catalyst (Degussa BLM 112W) was charged into a 100 cc autoclave, together with 12 g of ADN and 0.025 g of sodium diethyldithiocarbamide. Subsequently, 65 ml of liquid ammonia was added. The mixture was heated to 80° C., and reacted with hydrogen at a total pressure of 1000 psig (7.00 MPa). After 150 minutes, the yield of 6-aminocapronitrile reached ca. 70% at 89% ADN conversion for a selectivity of 79%.

EXAMPLE 13

1.2 g of sponge Ni catalyst (Degussa BLM 112W) was charged into a 100 cc autoclave, together with 0.05 g of selenophene, 12 g of ADN was injected into the autoclave and 65 ml of liquid ammonia was added. The mixture was heated to 80° C., and reacted with hydrogen at a total pressure of 1030 psig (7.00 MPa). After 480 minutes, the yield of 6-aminocapronitrile reached ca. 70% at 89% ADN conversion for a selectivity of 79%.

EXAMPLE 14

1.2 g of Raney® Co was charged into a 100 cc autoclave, together with 0.04 g of selenophene, 12 g of ADN was injected into the autoclave and 65 ml of liquid ammonia was added. The mixture was heated to 80° C., and reacted with hydrogen at a total pressure of 1030 psig (7.00 MPa). After 480 minutes, the yield of 6-aminocapronitrile reached ca. 68% at 83% ADN conversion for a selectivity of 82%.

EXAMPLE 15

1.2 g of a 5% rhodium on alumina catalyst (obtained from Engelhard) was charged into a 100 cc autoclave, together with 0.01 g of selenophene, 12 g of ADN was injected into the autoclave and 65 ml of liquid ammonia was added. The mixture was heated to 80° C., and reacted with hydrogen at a total pressure of 1000 psig (7.00 MPa). After 40 minutes, the yield of 6-aminocapronitrile reached ca. 70% at 92% ADN conversion for a selectivity of 76%.

What is claimed is:

1. A process for the partial hydrogenation of a dinitrile to an aminonitrile, comprising the step of contacting the dinitrile with a hydrogen-containing fluid in the presence of (a) a solvent comprising liquid ammonia, an alcohol or both; (b) a hydrogenation catalyst; and (c) an effective amount of an additive comprising a compound selected from the group consisting of a divalent sulfur and a divalent selenium compound.

2. The process of claim 1, wherein the dinitrile has the general formula $R(CN)_2$, wherein R is an alkylene group containing from 2 to 25 carbon atoms.

3. The process of claim 1, wherein the dinitrile is selected from the group consisting of adiponitrile, methylglutaronitrile and alpha,omega-dodecanedinitrile.

4. The process of claim 1, wherein the hydrogenation catalyst comprises a transition metal selected from the group consisting of iron, cobalt, nickel, rhodium and combinations thereof.

5. The process of claim 4, wherein the hydrogenation catalyst is in sponge metal form.

6. The process of claim 4, wherein the catalytic metal is supported on an inorganic support.

7. The process of claim 1, wherein the additive is selected from the group consisting of tetraalkylammonium polysulfide and sulfide compounds, thio and dithiocarbonyl compounds, and selenoaromatic compounds.

8. The process of claim 7, wherein the additive is selected from the group consisting of tetramethylammonium hydrogen sulfide; tetraethylammonium hydrogen sulfide; tetrapropylammonium hydrogen sulfide; tetrabutylammonium hydrogen sulfide; tetrabutylammonium hexasulfide; tetramethylthiourea; dimethylthioformamide; carbon disulfide; sodium diethyldithiocarbamide; zinc diethyldithiocarbamide; selenophene and its alkyl or aryl substituted derivatives; 1,3-selenazole and its alkyl and aryl substituted derivatives; and 1,2,3-selenadiazole and its alkyl and aryl substituted derivatives.

9. The process of claim 1, wherein the weight ratio of additive to hydrogenation catalyst is in the range of from about 0.01:1 to about 5:1.

10. The process of claim 1, wherein the dinitrile is selected from the group consisting of adiponitrile, methylglutaronitrile and alpha,omega-dodecanedinitrile; the hydrogenation catalyst comprises a transition metal selected from the group consisting of iron, cobalt, nickel, rhodium and combinations thereof; and the weight ratio of additive to hydrogenation catalyst is in the range of from about 0.01:1 to about 5:1.

11. The process of claim 7, wherein the dinitrile is selected from the group consisting of adiponitrile, methylglutaronitrile and alpha,omega-dodecanedinitrile; the hydrogenation catalyst comprises a transition metal selected from the group consisting of iron, cobalt, nickel, rhodium and combinations thereof; and the weight ratio of additive to hydrogenation catalyst is in the range of from about 0.01:1 to about 5:1.

12. The process of claim 8, wherein the dinitrile is selected from the group consisting of adiponitrile, methylglutaronitrile and alpha,omega-dodecanedinitrile; the hydrogenation catalyst comprises a transition metal selected from the group consisting of iron, cobalt, nickel, rhodium and combinations thereof; and the weight ratio of additive to hydrogenation catalyst is in the range of from about 0.01:1 to about 5:1.

13. An improved process for the preparing an aminonitrile from a corresponding dinitrile by contacting the dinitrile with a hydrogen-containing fluid in the presence of a solvent and a hydrogenation catalyst, wherein the improvement comprises contacting the dinitrile, hydrogen-containing fluid, solvent and hydrogenation catalyst in the further presence of an effective amount of an additive comprising a compound selected from the group consisting of a divalent sulfur and a divalent selenium compound.

14. The improved process of claim 13, wherein the additive is selected from the group consisting of tetraalkylammonium polysulfide and sulfide compounds, thio and dithiocarbonyl compounds, and selenoaromatic compounds.

15. The improved process of claim 14, wherein the additive is selected from the group consisting of tetramethylammonium hydrogen sulfide; tetraethylammonium hydrogen sulfide; tetrapropylammonium hydrogen sulfide; tetrabutylammonium hydrogen sulfide; tetrabutylammonium hexasulfide; tetramethylthiourea; dimethylthioformamide; carbon disulfide; sodium diethyldithiocarbamide; zinc diethyldithiocarbamide; selenophene and its alkyl or aryl substituted derivatives; 1,3-selenazole and its alkyl and aryl substituted derivatives; and 1,2,3-selenadiazole and its alkyl and aryl substituted derivatives.

16. The improved process of claim 13, wherein the dinitrile is selected from the group consisting of adiponitrile, methylglutaronitrile and alpha,omega-dodecanedinitrile; the hydrogenation catalyst comprises a transition metal selected from the group consisting of iron, cobalt, nickel, rhodium and combinations thereof; and the weight ratio of additive to hydrogenation catalyst is in the range of from about 0.01:1 to about 5:1.

17. A method for improving the yield of and/or selectivity to an aminonitrile obtained by partially hydrogenating a corresponding dinitrile with a hydrogen-containing fluid in the presence of a solvent and a hydrogenation catalyst, comprising the step of partially hydrogenating the dinitrile in the further presence of an effective amount of a compound selected from the group consisting of a divalent sulfur and a divalent selenium compound.

18. The method of claim 17, wherein the additive is selected from the group consisting of tetraalkylammonium polysulfide and sulfide compounds, thio and dithiocarbonyl compounds, and selenoaromatic compounds.

19. The method of claim 18, wherein the additive is selected from the group consisting of tetramethylammonium hydrogen sulfide; tetraethylammonium hydrogen sulfide; tetrapropylammonium hydrogen sulfide; tetrabutylammonium hydrogen sulfide; tetrabutylammonium hexasulfide; tetramethylthiourea; dimethylthioformamide; carbon disulfide; sodium diethyldithiocarbamide; zinc diethyldithiocarbamide; selenophene and its alkyl or aryl substituted derivatives; 1,3-selenazole and its alkyl and aryl substituted derivatives; and 1,2,3-selenadiazole and its alkyl and aryl substituted derivatives.

20. The method of claim 17, wherein the dinitrile is selected from the group consisting of adiponitrile, methylglutaronitrile and alpha,omega-dodecanedinitrile; the hydrogenation catalyst comprises a transition metal selected from the group consisting of iron, cobalt, nickel, rhodium and combinations thereof; and the weight ratio of additive to hydrogenation catalyst is in the range of from about 0.01:1 to about 5:1.

* * * * *